US010402538B2

(12) United States Patent
Dean

(10) Patent No.: US 10,402,538 B2
(45) Date of Patent: Sep. 3, 2019

(54) HEALTHCARE MANAGEMENT SYSTEM USING PATIENT PROFILE DATA

(71) Applicant: TriZetto Corporation, Denver, CO (US)

(72) Inventor: Val C. Dean, Franktown, CO (US)

(73) Assignee: Cognizant TriZetto Software Group, Inc., Englewood, CO (US)

( * ) Notice: Subject to any disclaimer, the term of this patent is extended or adjusted under 35 U.S.C. 154(b) by 1005 days.

(21) Appl. No.: 14/664,979

(22) Filed: Mar. 23, 2015

(65) Prior Publication Data

US 2015/0193582 A1 Jul. 9, 2015

Related U.S. Application Data

(63) Continuation of application No. 11/023,306, filed on Dec. 27, 2004, now abandoned.

(51) Int. Cl.
| | |
|---|---|
| *G06Q 10/00* | (2012.01) |
| *G06Q 50/00* | (2012.01) |
| *G06F 19/00* | (2018.01) |
| *G06Q 40/08* | (2012.01) |
| *G06Q 50/24* | (2012.01) |

(Continued)

(52) U.S. Cl.
CPC ........... *G06F 19/328* (2013.01); *G06Q 40/08* (2013.01); *G06Q 50/24* (2013.01); *G16H 10/60* (2018.01); *G16H 40/63* (2018.01)

(58) Field of Classification Search
CPC .............................. G06F 19/322; G06Q 50/24
See application file for complete search history.

(56) References Cited

U.S. PATENT DOCUMENTS

| 4,567,359 A | 1/1986 | Lockwood | 235/381 |
| 5,655,085 A | 8/1997 | Ryan et al. | 364/401 R |
| 5,903,889 A | 5/1999 | de la Huerga et al. | 707/3 |

(Continued)

FOREIGN PATENT DOCUMENTS

| WO | WO 94/20916 | 9/1994 | G06F 19/00 |
| WO | WO 01/69513 A2 | 9/2001 | G06F 19/00 |

OTHER PUBLICATIONS

International Search Report for Application No. PCT/US05/46464, dated Nov. 29, 2006, 5 pp.

(Continued)

*Primary Examiner* — Trang T Nguyen
(74) *Attorney, Agent, or Firm* — Dawn-Marie Bey; Bey & Cotropia PLLC

(57) ABSTRACT

The present disclosure is directed to a system and method which gathers information from all of a person's healthcare providers and abstracts from that information the data necessary for a healthcare provider to render informed medical decisions. In one embodiment, information necessary to process proper payment to a provider (re: reimbursement to the insured patient) is used to develop a holistic view of the medical condition pertaining to the patient. Since this information comes from a myriad of providers, including physicians, surgeons, nursing care, druggists, testing labs, mental health counselors, dentists, oral surgeons, etc., the holistic view that is developed is comprehensive. In one embodiment, the system and method could set parameters on critical data such that if that data is outside the set parameters, alerts can be sent to the appropriate caregivers and/or patients.

20 Claims, 2 Drawing Sheets

(51) Int. Cl.
*G16H 40/63* (2018.01)
*G16H 10/60* (2018.01)

(56) References Cited

U.S. PATENT DOCUMENTS

| | | | |
|---|---|---|---|
| 5,924,074 A | 7/1999 | Evans | 705/3 |
| 6,208,973 B1 | 3/2001 | Boyer et al. | 705/2 |
| 6,456,979 B1 | 9/2002 | Flagg | 705/4 |
| 7,346,522 B1 * | 3/2008 | Baylor | G06F 19/328 |
| | | | 235/380 |
| 2002/0010597 A1 | 1/2002 | Mayer et al. | 705/2 |
| 2002/0010679 A1 | 1/2002 | Felsher | 705/51 |
| 2002/0049617 A1 | 4/2002 | Lencki et al. | 705/4 |
| 2002/0111835 A1 | 8/2002 | Hele et al. | 705/4 |
| 2002/0147617 A1 | 10/2002 | Schoenbaum et al. | 705/4 |
| 2002/0147867 A1 | 10/2002 | Satlow | 710/100 |
| 2003/0036683 A1 | 2/2003 | Kehr et al. | 600/300 |
| 2003/0191667 A1 | 10/2003 | Fitzgerald et al. | 705/2 |
| 2003/0191669 A1 | 10/2003 | Fitzgerald et al. | 705/2 |
| 2004/0064343 A1 | 4/2004 | Korpman et al. | 705/2 |
| 2004/0078228 A1 * | 4/2004 | Fitzgerald | G06F 19/322 |
| | | | 705/2 |
| 2004/0117215 A1 | 6/2004 | Marchosky | 705/3 |
| 2004/0122790 A1 | 6/2004 | Walker et al. | 707/1 |
| 2004/0143462 A1 | 7/2004 | Hunt et al. | 705/3 |
| 2004/0205664 A1 | 10/2004 | Prendergast | 715/530 |
| 2004/0215494 A1 * | 10/2004 | Wahlbin | G06Q 40/02 |
| | | | 705/4 |
| 2005/0010446 A1 | 1/2005 | Lash et al. | 705/2 |
| 2005/0222867 A1 | 10/2005 | Underwood et al. | 705/2 |
| 2005/0246205 A1 * | 11/2005 | Wang | G16H 10/60 |
| | | | 705/3 |
| 2006/0071797 A1 * | 4/2006 | Rosenfeld | A61B 5/412 |
| | | | 340/573.1 |
| 2006/0080153 A1 * | 4/2006 | Fox | G06F 19/327 |
| | | | 705/4 |
| 2006/0136264 A1 | 6/2006 | Eaton et al. | 705/2 |

OTHER PUBLICATIONS

European Search Report issued for European Patent Application 05855083.1-2201, dated Jan. 17, 2008, 11 pp.
International Search Report and Written Opinion issued for PCT/US05/46461, dated Oct. 23, 2006.

* cited by examiner

HEALTHCARE MANAGEMENT SYSTEM USING PATIENT PROFILE DATA

CROSS-REFERENCE TO RELATED APPLICATIONS

The present application is a continuation of U.S. patent application Ser. No. 11/023,306, entitled "Healthcare management system using patient profile data" filed Dec. 27, 2004. The present application is related to concurrently filed, co-pending, and commonly assigned U.S. patent application Ser. No. 11/023,199, entitled "SYSTEM AND METHOD FOR SELECTING HEALTHCARE MANAGEMENT", filed Dec. 27, 2004, published as US 2006/0143040, Jun. 29, 2006, the disclosure of which is hereby incorporated by reference.

TECHNICAL FIELD

This invention is related to medical systems and more particularly to systems and methods for providing medical alerts based on consolidation of a patient's medical information.

BACKGROUND OF THE INVENTION

Healthcare providers, such as physicians, druggists, nurses, and even the patient himself or herself have only a limited view of health-related information pertaining to that patient which is necessary to make properly informed decisions. One limitation is the unavailability of the full range of data needed at a given time to make a fully informed medical decision. Another limitation is the inability to track data between different providers or between different visits to the same provider. For discussion, a visit is any contact with anyone in the chain of healthcare provision, including payors, claims processors, laboratories or pharmacists.

By way of example, assume a person visits a doctor with a particular problem. The doctor (assuming it's the patient's regular doctor) will know about chronic illnesses, such as diabetes, etc. of that patient. But what the doctor does not know is whether the patient has filled the last Rx and if he/she has, taken the medicine regularly. The healthcare provider may or may not know what other healthcare providers may have prescribed, and may or may not have lab test results ordered by other providers. Thus, when treatment is rendered it is done so without access to a wide body of knowledge pertaining to the patient.

Another problem with the scenario discussed above is that when the provider does make a decision on treatment, he/she then tells the patient to go off and do something and to call if there is a problem. Unless the patient calls with a problem, the provider does not have any insight into what is happening to the patient. This is not a prudent way to manage a person's health and is particularly troublesome when the patient has a chronic illness.

BRIEF SUMMARY OF THE INVENTION

The present disclosure is directed to a system and method which gathers information from all of a person's healthcare providers and abstracts from that information the data necessary for a healthcare provider to render informed medical decisions. In one embodiment, information necessary to process proper payment to a provider (re: reimbursement to the insured patient) is used to develop a holistic view of the medical condition pertaining to the patient. Since this information comes from a myriad of providers, including physicians, surgeons, nurse case managers, druggists, testing labs, mental health counselors, dentists, oral surgeons, etc., the holistic view that is developed is comprehensive.

In one embodiment, the system and method could set parameters on critical data such that if that data is outside the set parameters, alerts can be sent to the appropriate caregivers and/or patients.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

The forms which are filed (usually electronically) by healthcare providers for reimbursement from payors contain clinical data pertaining to the patient. In addition, health care plans use pharmacy benefit management companies (PBMs) to evaluate and pay pharmacy claims. This process of verification generates pharmacy data which then compliment the treatment and diagnostic data obtained from doctors. In addition, when a physician orders diagnostic tests, (laboratory, image, etc. tests), the test costs are billed for either by the ordering physician or by the providing physician, such as by a radiologist. The claim for payment also goes to the payor. In most situations the actual test results are available in electronic format and will also go the payor.

The system and method described herein takes advantage of the fact that all of this data funnels through a common point and can be used to provide a comprehensive holographic view of a patient's health. Thus, in the disclosed system and method, the health plan acts as the aggregator of information pertaining to its members and that aggregated information is used to create a meaningful representation of the medical profile of the member.

Figure 1:
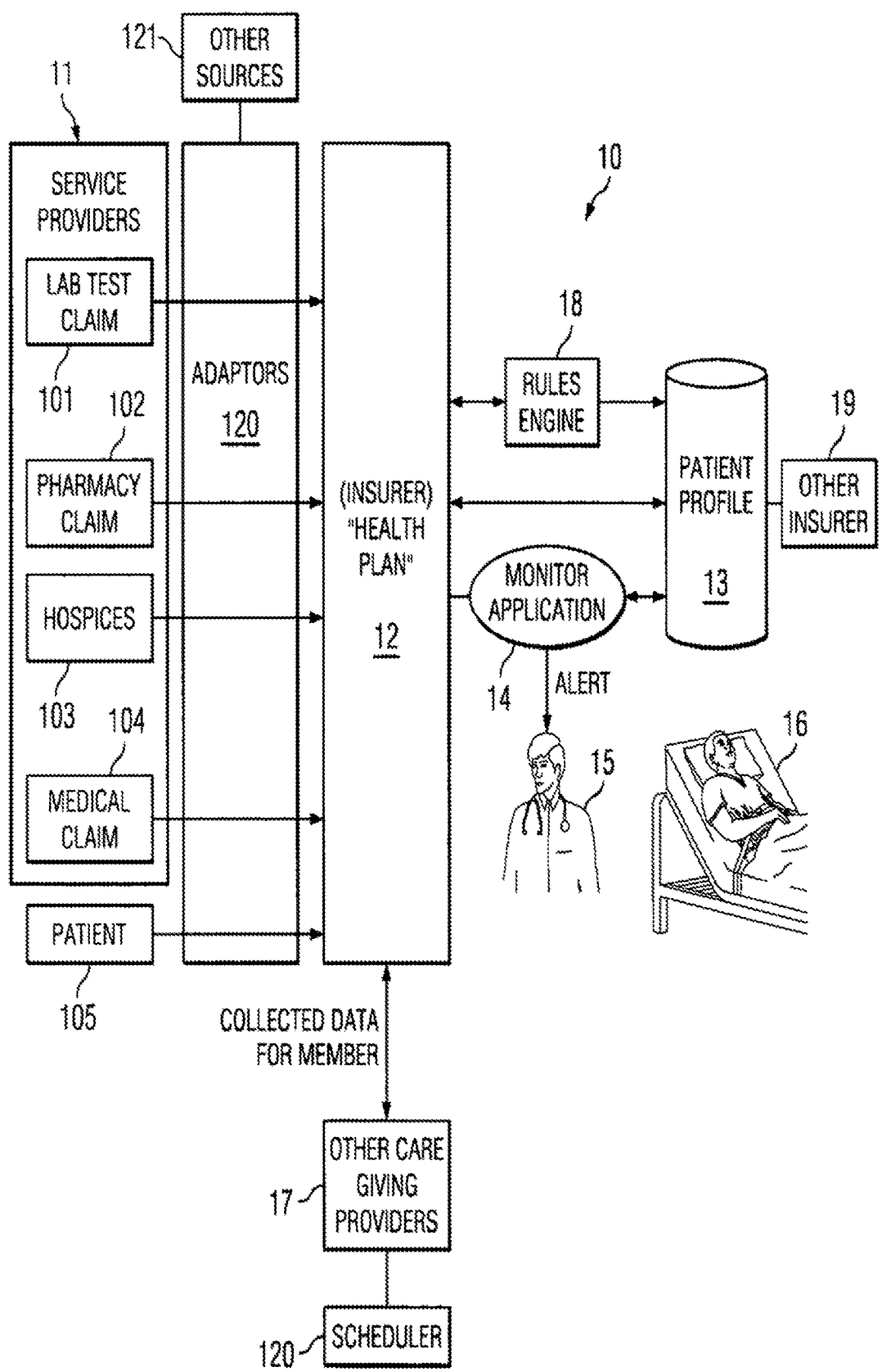
FIG. 1 is one embodiment of a system and method for consolidating medical information from a myriad of healthcare providers.

Turning now to FIG. 1, system 10 shows one embodiment of a system and method for consolidating medical information from diverse sources, such as Service Provider 11, to give a consolidated profile of a patient. Service provider 11 represents service providers which could encompass test lab 101, pharmacies 102, hospitals 103, and physicians 104. Claims from any provider are submitted to a patient's insurer 12. Others, such as the user, user's family, or even unrelated systems such as, for example, a credit card profile system, shown as 121. At least a portion of the information coming from these various diverse sources is stored in database 13. While it is contemplated that the raw data be stored in database 13 it could be that only abstracted data (such as above or below limit data) is so stored. Also note that database 13 could accept data from other insurers 19 which could occur, for example, if a patient were to have multiple insurers (husband and wife; private and government, etc.).

Assuming patient 16 used provider 15 as a primary provider but also used other providers 17 (cardiologist, diabetic specialist, obstetrician/gynecologist), it could be appropriate for any one or more of these providers to set "rules" for the patient. These rules could pertain to filling and refilling a prescription, taking and sending certain monitored readings (sugar levels, air flow, etc.), limits on certain readings, etc. These rules are stored in rules engine 18 on a patient-by-patient basis and when a rule has been attained (i.e., a certain monitored fact is outside a limit), then monitor application 14 sends a message, (e-mails, telephone, fax, etc.) to provider 15 (and possibly also to one or more other parties, including the patient).

Claims are submitted from various service providers, as well as the patient, and these claims may be formatted differently based on the reason for the data exchange. To handle such a situation, proper interfacing between systems is required and this is handled by adaptors, such as adapters 120.

One example of how the system and method could work is where physician A has prescribed a particular medication for a patient and physician B, possibly because that patient failed to inform physician B of the medication he/she is taking, prescribed another medication that might be dangerous when mixed with the first medication or possibly negates the effects of the first medication. In such a situation, the system would generate an alert to the patient and, if desired, to both physicians A and B. The reason the alert can be delivered is because of the composite view of a patient's medical history as obtained from payment records. Since the system is based upon data coming to a payor for reimbursement, over-the-counter medicines or medicines that are not paid for by the provider will only get into the system if the patient (or someone acting for the patient) sends in the data.

Another example would be if a patient has asthma and is asked to measure his/her peak air flow daily and to call the physician if the readings go below a certain level. Frequently patients don't follow through with the instructions or are worried about calling ("bothering") the physician. Using this system a member could go online to record his/her peak flow every day. This on-line data is then sent to the system. A rule is set up in the system that says: if air flow falls below a certain level, or if there is a significant downward trend, issue an alert. Thus, even if the patient is not at the critical stage, alerts are sent and trouble can be averted. The physician cannot take phone calls from patients every day and calculate changes to air flow, but the provider could set the system to accept a patient's input and to call (alerts) when certain limits are met. In addition, patients can input symptoms, such as coughing, vomiting, chest pain, headaches, temperature, blood pressure, etc., and this data can be used to trigger an alert based either on a general group rule, or on parameters set individually for that patient.

Compliance by a patient is another major concern. For example, the provider asks a patient to take a medication, monitor peak air flow to lungs, check blood sugar, see a specialist, etc. In reality, the provider does not know whether the patient has complied or not. When the patient ends up in the emergency room because of failure to follow directions it is often too late for help. However, using the system and method described herein, the provider will be notified if certain values decrease or change or hit a certain level. Alerts will be generated if the values are missing, i.e., not put in for two or three consistent days, etc. Also, missing data could be that a prescription has not been filled (or refilled on time), thereby initiating an alert.

These are all examples of the power obtained when the medical history of a patient can be generated and continually monitored based upon an abstraction of data meant for another purpose, namely payment information.

Figure 2:
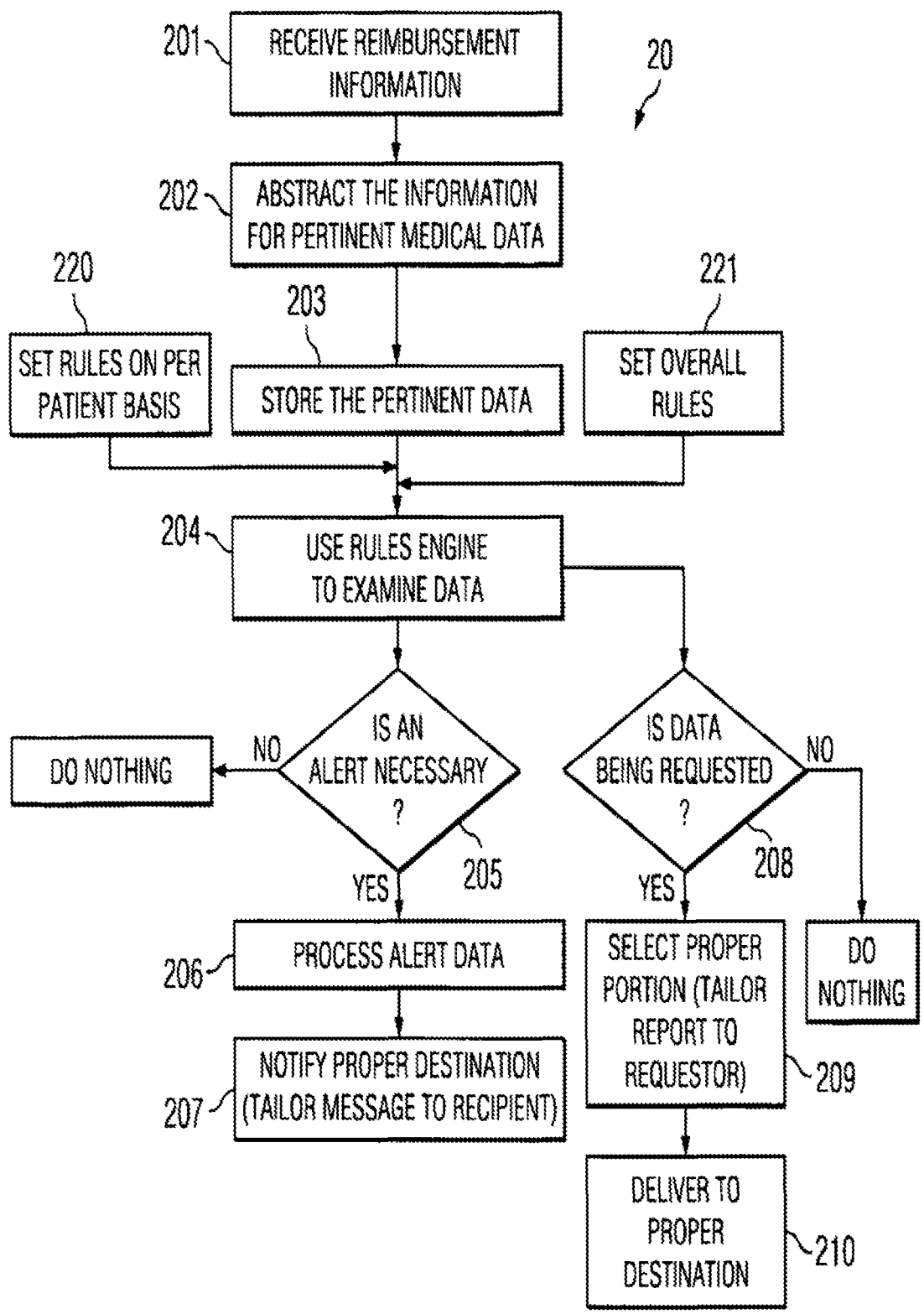
FIG. 2 is a flow chart of one embodiment of system operation.

FIG. 2 shows one embodiment of system 20 where process 201 receives reimbursement information (a payment claim) from any one of a number of medical providers. This information contains within it enough information so that the third party payor can process the payment to determine how much will be reimbursed. This reimbursement can be sent directly to the provider or sometimes it is sent to the patient. Each such claim must contain with it enough information so that the payor can properly determine the procedure that was performed, and whether the patient is eligible for reimbursement and what the limits are. Often the provider sends minimal information that certain tests have been performed and does not send the actual test results. However, in some situations, the actual test scores are sent with the payment claim information. Pharmacies send in the prescription and sometimes also the diagnosis along with their claim information. In FIG. 1 this information is shown coming from service providers 11 and goes directly to insurer 12 but the data could pass through adapters 120 designed such that the data from each provider is converted so that pertinent data can be removed, as desired, for storage in patient profile storage 13.

In addition, process 201 will process data from a patient, such as from patient 105 (FIG. 1). This data could be test results that have been self-administered, such as blood sugar levels, peak flow levels, blood pressure, temperature, or any other measurable physiological (or environmental) parameter that is necessary for a medical diagnosis. In addition a patient can input symptomatic information, such as chest pain, coughing, vomiting, or any other type of occurrence such as blurry vision, or abdominal pain, all of which will be received by process 201 and processed to become part of the patient profile information stored in storage 13.

Process 202, either before the information is stored in patient profile 13 or thereafter, and with or without the help of adaptors 120, creates an abstract of the information to determine certain information. For example, process 202 could look at various pieces of information and conclude that a patient is a diabetic. This would be concluded, for example, by looking at the medication the patient is taking, patient hospital visits, supplied lab test results, etc., and applying rules under control of rules engine 18 (FIG. 1) to conclude that this patient is in a group of diabetics. Other types of information could lead to an abstracting of a patient so that the patient is classified as a heart patient, a pregnant patient, etc. Each of these categories could then require the further abstracting of information to determine from symptoms provided by the patient when to send an alarm. The profile could be organized chronologically for all information, or chronologically for a particular test (such as MRIs) or could be organized in any manner desired. This profile could be made available to a provider or payor when desired and in the manner desired.

For example, if a patient is classified as having heart failure, then upon receiving information from a patient that the patient is having night time cough, the system would, based upon process 204, determine that this patient (or his/her health care provider) needs be alerted.

The system is established such that an administrator, who could be a doctor, could establish parameters that would apply to all of the patients in the database. This information would apply to the whole population of patients falling within the rules for the group. Within each group each physician could establish specific parameters for his/her specific patients.

Process 203, as discussed, stores the pertinent data either in patient profile storage 13 or in other storage and based upon rules established by rules engine 18. Process 205 determines if an alert is necessary. If an alert should be sent, such an alert will be processed via process 206 to determine what type of an alert, who the alert should go to, and how, and will also determine what type of data should be supplied. Process 207 sends the alert to one or more providers, other third parties, or to the patient, as desired.

Process 208 determines if data is being requested by a physician. This could occur, for example, if a patient shows up in an emergency room of a hospital seeking emergency care. An attending doctor then might request the system to provide an abstract of conditions that would be critical to know how to render proper informed medical assistance. For example, if the patient is diabetic, or is known to be on a medication to thin the blood, the doctor will be so informed. Note that sending a surgeon who is about to perform an operation an entire medical history of the patient is not what is required. What is required at this point is specific characterizations of the patient so that the surgeon can take proper steps. Process 209 handles this task. For example, the surgeon need not know the exact sugar levels over the last six months for this patient, but rather the surgeon needs to know that this patient is a diabetic and is on certain types of medication. Process 209 determines the proper data or portion of the data or abstract of the data and tailors the report to the requester based upon the nature of the request. Process 210 then delivers the report and data to the proper destination. This delivery both from process 210 or process 207 can be, for example, via the Internet or a telephone call or any other type of message, whether wireless or wire line.

There can also be continuous interaction between the patient and the system so that the patient or provider can set up personalized interventions or recommendations based upon clinical parameters. Thus, a reminder to refill a prescription (or to visit the caregiver or a specialist), can be sent to a patient when a prescription is not filled on time or when a suggested specialist has not been visited. Actual insurance reimbursement for future medical visits could, if desired, be dependent upon compliance. Notification to a patient may, for instance, be sent to a patient that he/she should not take both of the drugs prescribed (perhaps by different doctors) because one of the drugs has the ingredients of the other. Based on the severity of that situation (for example, two drugs prescribed which are contra-indicated for use with each other), it may be desired to send a message to the caregiver.

Messages could be delivered warning a patient of expected symptoms when certain medication, or combination of medications, are being taken. Also, post-operative suggestions can be sent to patients who have just had a certain procedure performed. In some situations preliminary diagnosis is possible based upon all of the information that is available. For example, assume a patient (or a provider) enters into the system (either directly or abstracted from a claims form) a certain set of symptoms. Assume also that these symptoms suggest a disease known to be prevalent in a certain part of the world. The system then could examine the travel records (as obtained from credit card abstracts or airline records) and note to the provider (or to the patient) the fact that the symptoms may be related to the patient's recent trip to a certain country.

Note that any such message must be HIPAA compliant and thus secure e-mail, personal telephone calls, may be necessary. Also note that the message can take any form, such as "Dear Patient, we do not see that you have reordered your XYZ medication. If there is a problem, please call us or please refill it now. Thanks, Your Doctor." If the prescription remains unfilled on day five, an alert would go to the doctor as an indication that perhaps the doctor needs to call the patient to see what is going on.

Rules could be, for example, entered into the database to the effect that all males over the age of 50 who have not had a PSA in the last year are identified. Based on such a rule, alerts would be sent to each identified patient and to each patient's provider. For those patients who must be seen by a provider at periodic times, reminders can be sent and these reminders could, if desired, already have attached a scheduled provider visit. This could, for example, be accomplished using scheduler 120 (FIG. 1) which would be updated (or synchronized) by each provider's office in the same manner as synchronism occurs in PDA calendars.

While it would always be best to have a complete file, including x-rays, MRIs, lab tests, etc., accessible for a patient when any diagnosis is being made, this would be the exception and not the rule. A next best situation would be if a profile of the patient could be made available. That profile is then made up of data indicating certain important factors. For example, if a medical history of visits, drugs and tests indicates a patient is a diabetic, then a provider may only be told the patient is a diabetic and all of the hundreds of test results would not be sent. This abstract profile is, as discussed above, determined by looking at prescriptions, doctors visited and lab tests, as obtained from payment records. Note that simply giving a printout (electronic or otherwise) of all tests, provider visits, etc., is overwhelming and not helpful, but providing the proper level of detailed information can be very helpful.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for providing a medical alert using consolidated medical information for an individual from multiple sources aggregated continually at a common point, said method comprising:
   receiving by adaptors of a reimbursement system multiple claims for reimbursement, wherein each of the multiple claims for reimbursement is from a different medical service provider and each of the multiple claims for reimbursement pertains to a medical service provided to the individual and further wherein, each of the multiple claims is in a different data exchange format and a different adaptor is provided for each of the different data exchange formats;
   abstracting by the adaptors from each of the multiple received claims each of the following first portions of information if included in the received claim: medical test results for the individual, prescription information for the individual, medical diagnosis information for the individual, wherein the abstracted first portions are converted from each of the different data exchange formats and provided by the adaptors to a rules engine;
   processing the abstracted first portions of information by a rules engine against one or more overall rules for identifying health-related diagnoses stored therein to determine if the abstracted first portions of information support identify the individual as a patient with one or more health-related diagnose;
   storing the first abstracted portions as consolidated medical information for the individual in a database of the reimbursement system in accordance with any identified one or more health-related diagnoses;
   storing in the rules engine of the reimbursement system one or more specific rule sets provided by one or more of the different medical service providers, wherein each of the one or more specific rule sets is specific to the individual;
   receiving by the adaptors of the reimbursement system at least one additional claim pertaining to the individual after storage of the consolidated medical information in the database and storage of the overall rules and one or more specific rules sets;
   abstracting by the adaptors from the at least one additional claim each of the following second portions of information if included in the received at least one additional claim: medical test results for the individual, prescription information for the individual, medical diagnosis information for the individual, symptoms being experienced by the individual, over-the-counter medication taken by the individual;
   processing the abstracted second portions of information by the rules engine against the one or more overall rules for identifying health-related diagnoses stored therein to determine if the abstracted second portions of information support identify the individual as a patient with one or more additional health-related diagnoses; and
   examining by the rules engine the abstracted second portions of information by applying the one or more specific rule sets thereto;
   determining from the processing and examination that at least one of the overall rules and the one or more specific customer rules has been attained and that an alert is necessary;
   generating by a monitor application of the reimbursement system an alert to one or more of the multiple providers and the individual, wherein the alert is related the individual's one or more health-related diagnoses; and
   receiving from the adaptors, each of the multiple claims for reimbursement at a payor, determining a reimbursement amount and sending determined reimbursement amounts to each of the different medical service providers.

2. The method according to claim 1, further comprising:
   updating the consolidated medical information of the individual by storing the second abstracted portions in the database of the reimbursement system to include the individual's one or more health-related diagnoses.

3. The method according to claim 1, wherein the at least one additional claim pertaining to the individual is received by the adaptors from the individual.

4. The method according to claim 1, wherein the at least one additional claim pertaining to the individual is received by the adaptors from one of the multiple service providers.

5. The method according to claim 1, wherein the at least one additional claim pertaining to the individual is received by the adaptors from a new service provider.

6. The method according to claim 1, further comprising receiving by the adaptors additional medical information for the individual from a credit card profile system.

7. A method for providing a medical alert using medical information for an individual from multiple sources aggregated continually at a common point, said method comprising:
   storing in a rules engine of a reimbursement system overall rules for identifying health-related diagnoses;
   receiving by adaptors of a reimbursement system multiple claims for reimbursement, wherein each of the multiple claims for reimbursement is from a different medical service provider and each of the multiple claims for reimbursement pertains to a medical service provided to the individual and further wherein, each of the multiple claims is in a different data exchange format and a different adaptor is provided for each of the different data exchange formats;
   abstracting by the adaptors from each of the multiple received claims each of the following first portions of information if included in the received claim: medical test results for the individual, prescription information for the individual, medical diagnosis information for the individual, wherein the abstracted first portions are converted from each of the different data exchange formats and provided by the adaptors to a rules engine;
   processing the abstracted first portions of information to determine if the abstracted first portions of information support identify the individual as a patient with one or more health-related diagnoses;
   determining from the processing that at least one of the overall rules has been attained and that an alert is necessary;
   generating by a monitor application of the reimbursement system an alert to one or more of the multiple providers and the individual, wherein the alert is related the individual's one or more health-related diagnoses; and
   receiving from the adaptors, each of the multiple claims for reimbursement at a payor, determining a reimbursement amount and sending determined reimbursement amounts to each of the different medical service providers.

8. The method according to claim 7, further comprising storing the first abstracted portions as consolidated medical information for the individual in a database of the reimbursement system to include the individual's one or more health-related diagnoses.

9. The method according to claim 8, further comprising;
receiving by the adaptors of the reimbursement system at least one additional claim pertaining to the individual after storage of the consolidated medical information in the database and storage of the overall rules in the rules engine;
abstracting by the adaptors from the at least one additional claim each of the following second portions of information if included in the received at least one additional claim: medical test results for the individual, prescription information for the individual, medical diagnosis information for the individual, symptoms being experienced by the individual, over-the-counter medication taken by the individual, wherein the abstracted second portions are converted from each of the different data exchange formats and provided by the adaptors to a rules engine;
processing the abstracted second portions of information by the rules engine against the one or more overall rules for identifying health-related diagnoses stored therein to determine if the abstracted second portions of information support identifying the individual as a patient with one or more additional health-related diagnoses;
determining from the processing that at least one of the overall rules has been attained and that an alert is necessary;
generating by the monitor application an alert to one or more of the multiple providers and the individual, wherein the alert is related the individual's one or more health-related diagnoses; and
updating the consolidated medical information of the individual by storing the second abstracted portions in the database of the reimbursement system to include the individual's one or more health-related diagnoses.

10. The method according to claim 9, wherein the at least one additional claim pertaining to the individual is received by the adaptors from the individual.

11. The method according to claim 9, wherein the at least one additional claim pertaining to the individual is received by the adaptors from one of the multiple service providers.

12. The method according to claim 9, wherein the at least one additional claim pertaining to the individual is received by the adaptors from a new service provider.

13. The method according to claim 9, further comprising receiving by the adaptors additional medical information for the individual from a credit card profile system.

14. A method for providing a medical alert using consolidated medical information for an individual from multiple sources aggregated continually at a common point, said method comprising:
receiving by adaptors of a reimbursement system multiple claims for reimbursement, wherein each of the multiple claims for reimbursement is from a different medical service provider and each of the multiple claims for reimbursement pertains to a medical service provided to the individual and further wherein, each of the multiple claims is in a different data exchange format and a different adaptor is provided for each of the different data exchange formats;
abstracting by the adaptors from each of the multiple received claims each of the following first portions of information if included in the received claim: medical test results for the individual, prescription information for the individual, medical diagnosis information for the individual, wherein the abstracted first portions are converted from each of the different data exchange formats and provided by the adaptors to a rules engine;
processing the abstracted first portions of information by a rules engine against one or more overall rules for identifying health-related diagnoses stored therein to determine if the abstracted first portions of information support identifying the individual as a patient with one or more health-related diagnoses;
storing the first abstracted portions as consolidated medical information for the individual in a database of the reimbursement system in accordance with any identified one or more health-related diagnoses;
storing in the rules engine of the reimbursement system one or more specific rule sets provided by one or more of the different medical service providers, wherein each of the one or more specific rule sets is specific to the individual and is related to the individual's one or more health-related diagnoses;
receiving by the adaptors of the reimbursement system at least one additional claim pertaining to the individual after storage of the consolidated medical information in the database and storage of the one or more specific rules sets in the rules engine;
abstracting by the adaptors from the at least one additional claim each of the following second portions of information if included in the received at least one additional claim: medical test results for the individual, prescription information for the individual, medical diagnosis information for the individual, symptoms being experienced by the individual, over-the-counter medication taken by the individual;
processing the abstracted second portions of information by the rules engine against the one or more overall rules for identifying health-related diagnoses stored therein to determine if the abstracted second portions of information support identifying the individual as a patient with one or more additional health-related diagnoses; and
examining by the rules engine the abstracted second portions of information by applying the one or more specific rule sets thereto;
determining from the processing and examination that at least one of the one or more specific rules has been attained and that an alert is necessary; and
generating by a monitor application of the reimbursement system an alert to one or more of the multiple providers and the individual, wherein the alert is related the individual's one or more health-related diagnoses; and
receiving from the adaptors, each of the multiple claims for reimbursement at a payor, determining a reimbursement amount and sending determined reimbursement amounts to each of the different medical service providers.

15. The method according to claim 14, further comprising:
updating the consolidated medical information of the individual by storing the second abstracted portions in the database of the reimbursement system to include the individual's one or more health-related diagnoses.

16. The method according to claim 14, wherein the at least one additional claim pertaining to the individual is received by the adaptors from the individual.

17. The method according to claim 14, wherein the at least one additional claim pertaining to the individual is received by the adaptors from one of the multiple service providers.

18. The method according to claim 14, wherein the at least one additional claim pertaining to the individual is received by the adaptors from a new service provider.

19. The method according to claim 14, further comprising receiving by the adaptors additional medical information for the individual from a credit card profile system, wherein the additional medical information is examined in accordance with the specific rule sets to determine if an alert is necessary.

20. The method according to claim 14, further comprising receiving by and saving in the database further health-related data for the individual from a different reimbursement system, wherein the further health-related data is examined in accordance with the specific rule sets to determine if an alert is necessary.

\* \* \* \* \*